US00PP20815P2

(12) United States Plant Patent
Perkins

(10) Patent No.: US PP20,815 P2
(45) Date of Patent: Mar. 9, 2010

(54) *ANGELONIA* PLANT NAMED 'CAR LAVER09'
(50) Latin Name: *Angelonia angustifolia*
Varietal Denomination: Car Laver09

(75) Inventor: Ralph T. Perkins, Gilroy, CA (US)
(73) Assignee: Syngenta Crop Protection AG, Basel (CH)

( * ) Notice: Subject to any disclaimer, the term of this patent is extended or adjusted under 35 U.S.C. 154(b) by 0 days.
(21) Appl. No.: 12/316,965
(22) Filed: Dec. 18, 2008
(51) Int. Cl.
*A01H 5/00* (2006.01)
(52) U.S. Cl. ..... Plt./404
(58) Field of Classification Search ..... Plt./263, Plt./404
See application file for complete search history.
*Primary Examiner*—Susan B McCormick Ewoldt
(74) *Attorney, Agent, or Firm*—S. Matthew Edwards

(57) ABSTRACT

A new *Angelonia* plant named 'Car Laver09,' particularly distinguished by violet flower color, upright and medium-compact habit, dense foliage, strong stems, and good floriferousness.

1 Drawing Sheet

Latin name of the genus and species of the plant claimed: *Angelonia angustifolia.*

Varietal denomination: 'Car Laver09'.

BACKGROUND OF THE NEW PLANT

The present invention comprises a new *Angelonia,* botanically known as *Angelonia angustifolia* and hereinafter referred to by the variety name 'Car Laver09.'

'Car Laver09' is a product of a planned breeding program. The new cultivar 'Car Laver09' has a violet flower color, upright and medium-compact habit with dense foliage, strong stems, and good floriferousness.

'Car Laver09' originated from a hybridization in a controlled breeding program in Gilroy, Calif. U.S.A. The female parent was an unpatented hybrid seedling identified as '148-3' with lavender color. '148-3' has a darker lavender color, taller plant habit, and is less floriferious than 'Car Laver09.'

The male parent of 'Car Laver09' was an unpatented hybrid seedling identified as '257-5' with lavender color. '257-5' has a darker flower color, less branching, and is less floriferious than 'Car Laver09.'

'Car Laver09' was selected as one flowering plant within the progeny of the stated cross in July 2003 in a controlled environment in Gilroy, Calif. U.S.A.

The first act of asexual reproduction of 'Car Laver09' was accomplished when vegetative cuttings taken from the initial selection in July 2003 in a controlled environment in Gilroy, Calif. U.S.A. The pollination took place in October 2002 and the seed sowing in April 2003 all in Gilroy, Calif., U.S.A.

Horticultural examination of plants grown from cuttings of the plant initiated in July 2003 in Gilroy, Calif. U.S.A., and continuing thereafter, has demonstrated that the combination of characteristics as herein disclosed for 'Car Laver09' are firmly fixed and are retained through successive generations of asexual reproduction.

'Car Laver09' has not been observed under all possible environmental conditions. The phenotype may vary significantly with variations in environment such as temperature, light intensity and day length.

A Plant Breeder's Right for this cultivar was applied for in Canada on Dec. 24, 2007. 'Car Laver09' has not been made publicly available more than one year prior to the filing of this application.

DESCRIPTION OF THE DRAWINGS

The accompanying photographic drawing shows typical flower and foliage characteristics of 'Car Laver09' with colors being as true as possible with an illustration of this type. The photographic drawing shows a flowering plant of the new variety grown in a field trial in Gilroy, Calif. U.S.A. in August 2007.

DETAILED BOTANICAL DESCRIPTION

The measurements were taken in Gilroy, Calif. U.S.A. in June 2008 on plants that were growing in gallon pots. These plants were approximately 6 months old.

Color Chart used: Royal Horticultural Society Colour Chart (R.H.S.) 2001.

BRIEF SUMMARY OF INVENTION

The following observations, measurements, and comparisons describe plants grown outside in Gilroy, Calif. U.S.A. The following traits have been repeatedly observed and are determined to be basic characteristics of the new variety. The combination of these characteristics distinguishes this *Angelonia* as a new and distinct variety.

TABLE 1

DIFFERENCES BETWEEN THE NEW VARIETY 'CAR LAVER09' AND A SIMILAR VARIETY

| | 'Car Laver09' | 'Balanglavup' |
|---|---|---|
| Plant habit | Broader and shorter | Narrower and taller |
| Foliage color | Darker stem and foliage | Lighter stems and foliage |
| Foliage size | Larger | Smaller |

Plant:

*Form, growth and habit.*—Upright and medium-compact habit, dense foliage, and strong stems.

*Plant height.*—38–42 cm.

*Plant height* (*inflorescence included*).—41–46 cm.

*Plant width.*—40–50 cm.

Foliage:

*Immature, leaf color, upper surface.*—RHS 137A.

*Lower surface.*—RHS 137C.

*Mature, leaf color, upper surface.*—Darker than RHS 137A.
*Lower surface.*—RHS 137C.
*Length.*6.3–7.5 cm.
*Width.*—0.9–1.0 cm.
*Shape.*—Elliptical.
*Base shape.*—Cuncate.
*Apex shape.*—Acute.
*Margin.*—Serrate.
*Texture.*—Glandular hairs.
*Color of veins, upper and lower surfaces.*—RHS 144A.

Stem:
*Number of main stems per plant.*—About 6.
*Number of leaves per stem.*—10–14.
*Color of stem.*—RHS 144A.
*Length of stem.*—30–35 cm.
*Diameter.*—0.3–0.4 cm.
*Length of internodes.*—1.7–2.5 cm.
*Texture.*—Glandular hairs.

Inflorescence:
*Type.*—Terminal raceme florets, solitary in leaf axils, sometimes appear alternate or opposite.
*Number of florets per raceme.*—20–30.
*Raceme length.*—12–15 cm.
*Color of pedicel.*—RHS 144A basally; with anthocyanins of RHS 178A towards the apex.
*Length of pedicel.*—1.7–2.5 cm.
*Diameter of pedicel.*—0.1 cm.
*Texture.*—Many glandular hairs.

Corolla:
*Form.*—Single, two-lipped (5-petaled, fused at base).
*Length of floret.*—2.2–2.4 cm.
*Width of floret.*—2.1–2.3 cm.
*Color, upper lip petals, upper surface.*—RHS N87A; fading to RHS N87B at the corolla opening.
*Color, upper lip petals, lower surface.*—RHS N87B to C.
*Size, upper lip petal length.*—0.7 cm from corolla opening.
*Color lower lip, lateral petals, upper surface.*—RHS N87B at the outer portion; RHS N87C at the corolla opening.
*Color lower lip, lateral petals, lower surface.*—RHS N87B to C.
*Size lower lip, lateral petals length.*—0.8–0.9 cm from corolla opening.
*Size lower lip, lateral petals width.*—0.9–1.2 cm.
*Color lower lip, mid-petal, upper surface.*—Mostly RHS N87C with a few slight blotches of RHS N87B; RHS N155B with RHS 144A basally.
*Color lower lip, mid-petal, lower surface.*—RHS N87C.
*Size lower lip, mid-petal length.*—1.1–1.2 cm from corolla opening.
*Size lower lip, mid-petal width.*—0.9 cm.
*Petal shape.*—Obovate.
*Apex shape.*—Rounded.
*Margin.*—Papillose and glandular hairs on both surfaces.
*Corolla color, inside.*—RHS N155B ground color, with a little overlaid color of RHS N87C; RHS N79B spots.
*Corolla color, outside.*—RHS N155B ground color, with a little overlaid color of RHS N87C–D; RHS N77B spots.
*Duration of flowering.*—Continuous flowering throughout the Summer.
*Fragrance.*—None.
*Lastingness of individual florets.*—About 6–7 days.

Bud (just before opening):
*Color.*—RHS N187B.
*Length.*—1.0–1.2 cm.
*Width.*—0.6–0.7 cm.
*Shape.*—Obicular.
*Number of sepals.*—5, fused at base.
*Color of sepals.*—RHS 147A.
*Length of sepals.*—0.3–0.5 cm.
*Width of sepals.*—0.1 cm.
*Sepal shape.*—Lanceolate.
*Apex shape.*—Acute.
*Margins.*—Entire.
*Texture.*—Glabrous, both sides.

Reproductive organs:
*Pistil.*—1.
*Length.*—0.3–0.4 cm.
*Style color.*—RHS N155B but whiter.
*Stigma color.*—RHS N155B but whiter with a RHS 144A tip.
*Number of stamens.*—4, in pairs.
*Length filaments.*—0.4 cm.
*Color of filaments.*—RHS N155B but whiter.
*Color of pollen.*—RHS N155A.
*Pollen amount.*—Very scarce.
*Fertility/seed set.*—Not observed on this hybrid.

Disease/pest resistance: Disease resistance or susceptibility has not been observed on this hybrid.

What is claimed is:

1. A new and distinct variety of *Angelonia* plant named 'Car Laver09,' substantially as illustrated and described herein.

* * * * *

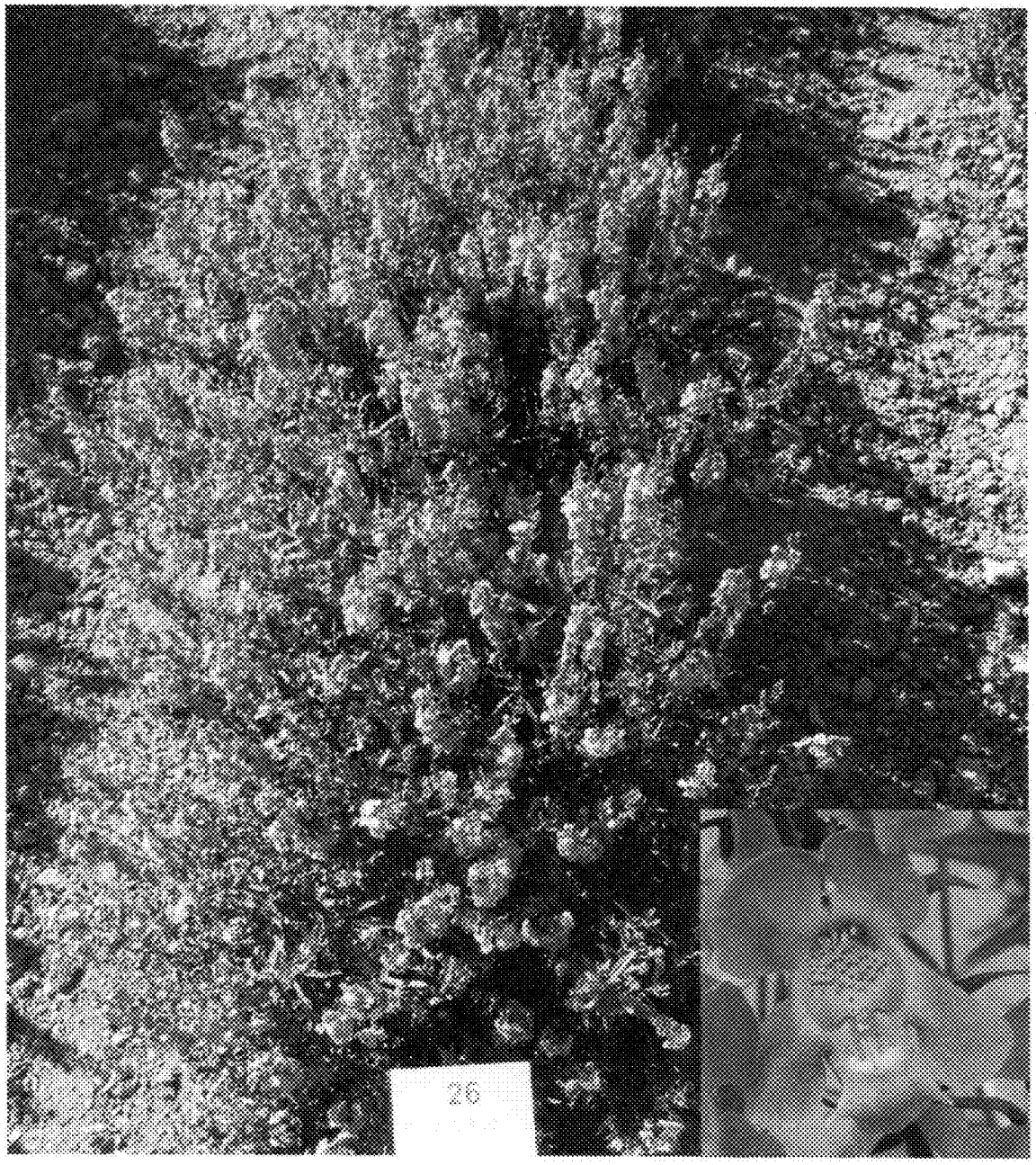
2G